US007479505B2

(12) United States Patent
Calabresi et al.

(10) Patent No.: US 7,479,505 B2
(45) Date of Patent: *Jan. 20, 2009

(54) USE OF TAUROLIDINE TO TREAT TUMORS

(75) Inventors: Paul Calabresi, Barrington, RI (US); James Darnowski, Barrington, RI (US)

(73) Assignee: Geistlich Phama AG, Wolhusen (CH)

(*) Notice: Subject to any disclaimer, the term of this patent is extended or adjusted under 35 U.S.C. 154(b) by 242 days.

This patent is subject to a terminal disclaimer.

(21) Appl. No.: 10/796,861

(22) Filed: Mar. 8, 2004

(65) Prior Publication Data

US 2004/0176360 A1 Sep. 9, 2004

(51) Int. Cl.
*A61K 31/54* (2006.01)
*A61K 45/05* (2006.01)

(52) U.S. Cl. .................. 514/422; 514/538; 514/56; 514/222.5; 514/885; 424/85.1

(58) Field of Classification Search .................. 514/422, 514/538, 56, 222.5, 885; 424/85.1
See application file for complete search history.

(56) References Cited

U.S. PATENT DOCUMENTS

| 3,423,408 | A | 1/1969 | Pfirrmann ............... 260/243 |
| 3,963,706 | A | 6/1976 | Pfirrmann ............... 260/239.9 |
| 4,096,241 | A | 6/1978 | Geistlich et al. ............... 424/54 |
| 4,107,305 | A | 8/1978 | Pfirrmann ............... 424/246 |
| 4,226,858 | A | 10/1980 | Pfirrmann ............... 424/195 |
| 4,337,251 | A | 6/1982 | Pfirrmann ............... 424/246 |
| 4,587,268 | A | 5/1986 | Pfirrmann ............... 514/774 |
| 4,604,391 | A | 8/1986 | Pfirrmann ............... 514/222 |
| 4,626,536 | A | 12/1986 | Pfirrmann ............... 514/222 |
| 4,772,468 | A | 9/1988 | Pfirrmann ............... 424/128 |
| 5,210,083 | A | 5/1993 | Pfirrmann ............... 514/222.5 |
| 5,573,771 | A | 11/1996 | Geistlich et al. ............... 424/422 |
| 5,593,665 | A | 1/1997 | Pfirrmann et al. ............... 424/85.1 |
| 5,661,179 | A * | 8/1997 | Samid ............... 514/538 |
| 5,819,748 | A | 10/1998 | Pfirrmann ............... 128/898 |
| 5,954,687 | A | 9/1999 | Baudino ............... 604/48 |
| 5,972,933 | A | 10/1999 | Pfirrmann ............... 514/222.5 |
| 5,976,822 | A | 11/1999 | Landrum et al. ............... 435/23 |
| 6,011,030 | A | 1/2000 | Pfirrmann ............... 514/222.2 |
| 6,080,397 | A | 6/2000 | Pfirrmann et al. ............... 424/78.08 |
| 6,117,868 | A | 9/2000 | Pfirrmann ............... 514/222.5 |
| 6,303,596 | B1 | 10/2001 | Morrissey et al. ............... 514/222.5 |
| 6,429,224 | B1 * | 8/2002 | Calabresi et al. ............... 514/422 |
| 6,479,481 | B1 * | 11/2002 | Stendel et al. ............... 514/222.5 |
| 6,703,413 | B2 * | 3/2004 | Calabresi et al. ............... 514/422 |
| 6,812,251 | B2 * | 11/2004 | Calabresi et al. ............... 514/601 |
| 6,995,164 | B2 * | 2/2006 | Calabresi et al. ............... 514/263.32 |
| 2005/0065122 | A1 * | 3/2005 | Calabresi et al. ............... 514/151 |
| 2006/0135513 | A1 * | 6/2006 | Calabresi et al. ............... 514/222.5 |

FOREIGN PATENT DOCUMENTS

| EP | 0253662 | 1/1988 |
| EP | 1066830 | 1/2001 |
| WO | WO 90/06138 | 5/1990 |
| WO | WO 9006138 | 6/1990 |
| WO | WO 91/13628 | 9/1991 |
| WO | WO 92/00743 | 1/1992 |
| WO | WO 94/03174 | 2/1994 |
| WO | WO 9403174 | 2/1994 |
| WO | WO 98/52572 | 11/1998 |
| WO | WO 99/06114 | 2/1999 |
| WO | WO 99/34805 | 7/1999 |

OTHER PUBLICATIONS

Blenkharn et al. (1987) "The Antibacterial and Anti-Endotoxin Activity of Taurolidine in Combination with Antibiotics," Surg. Res. Commun., 2:149-155.
Browne M.K. et al. (1985) "Studies on the Antiendotoxin Properties of Taurolin in Animals and Man," *Recent Advances in Chemotherapy*, Proceedings of the 14th International Congress of Chemotherapy, Kyoto, pp. 2075-2076.
Browne M.K. et al. (1976) "Taurolin, a New Chemotheraputic Agent," *The Journal of Applied Bacteriology*, vol. 41, pp. 363-368.
Geistlich Catalog, "Taurolin, Triad antimicrobial chemotherapy" pp. 1-95.
Gorman et al. (1987) "Reduced Adherence of Micro -Organisms to Human Mucosal Epithelial Cells Following Treatment with Taurolin, a Novel Antimicrobial Agent," J. App. Bacteriol., 62:315-320.
Hamik, A. et al. (1997) "Taurolidine Inhibits Tissue Factor Expression in Monocytes," *Abstract from the XVIth Congress of the International Society on Thrombosis and Haemostasis*, Florence, Jun. 6-12.
Jacobi, C. et al. (1999) "New Therapeutic Strategies to Avoid Intra- and Extraperitoneal Metastases during Laparoscopy: Results of a Tumor Model in the Rat," *Digestive Surgery*, vol. 16 (5), pp. 393-399.
Jacobi, C. et al. (1997) "Inhibition of Peritoneal Tumor Cell Growth and Implantation in Laparoscopic Surgery in a Rat Model," *The American Journal of Surgery*, vol. 174 (3), pp. 359-363.
Jacobi, C. et al. (1999) "Influence of Different Gases and Intraperitoneal Instillation of Antiadherent of Cytotoxic Agents on Peritoneal Tumor Cell Growth and Implantation with Laproscopic Surgery in a Rat Model," *Surg. Endos*. 13:1021-25.
Knight et al., (1983) "NMR Studies and GC Analysis of the Antibacterial Agent Taurolidine," J. Pharm. Sci. 72:705-707.
Leaper et al. (1985) "Prevention of peritoneal adhesions after thermal injury using the formaldehyde carriers noxythidin and Taurolin", *Br. Soc. Gastroenterology*, p. A901.
McCourt, M. et al. (2000) "Taurolidine Inhibits Tumor Cell Growth In Vitro and In Vivo." *Annals of Surgical Oncology*, vol. 7(9), pp. 685-691.
Monson, J.R.T. et al. (1990) "Preliminary evidence that taurolidine is anti-neoplastic as well as anti-endotoxin and anti-microbial," *The British Journal of Surgery*. vol. 77(6), pp. 711.

(Continued)

Primary Examiner—Mina Haghighatian
(74) Attorney, Agent, or Firm—Rothwell, Figg, Ernst & Manbeck, P.C.

(57) ABSTRACT

The invention provides a method of inhibiting tumor growth in a mammal, by administering to the mammal composition containing taurolidine, taurultam, or a biologically active derivative thereof. The composition is administered to directly contact a tumor cell at a dose sufficient to induce cell death by apoptosis.

24 Claims, 6 Drawing Sheets

OTHER PUBLICATIONS

Monson, J.R.T. et al., (1993) "Taurolidine inhibits tumor necrosis factor (TNR) toxicity new evidence of TNF and endotoxin synergy," *European Journal of Surgical Oncology*, 19:226-231.

Reymond, M.A. et al. (2000) "Feasibility of therapeutic pneumoperitoneum in a large animal model using a microvaporisator," *Surgical Endoscopy*, vol. 14(1), pp. 51-55.

Umpleby, H. et al. (1984) "The efficacy of agents employed to prevent anastomotic recurrence in colorectal carcinoma," *Annals of the Royal College of Surgeons of England*, 66:192-194.

Volz J. et al. (2000) "Modulation of Tumor-Induced Lethality after Pneumoperitoneum in a Mouse Model," *Cancer*, vol. 89(2), pp. 262-266.

Wicki, O. et al, (1983) "Solution for Surgical Lavage," *Langenbecks Archiv für Chirurgie*, p. 778, Abstract 276.

International Search Report for PCT/US00/33103, mailed Dec. 3, 2001.

International Search Report.

* cited by examiner

USE OF TAUROLIDINE TO TREAT TUMORS

RELATED APPLICATION

This application claims the benefit from provisional application Ser. No. 60/169,122, which was filed on Dec. 6, 1999, provisional application Ser. No. 60/169,127, which was filed on Dec. 6, 1999, and provisional application Ser. No. 60/169,128, which was filed on Dec. 6, 1999.

BACKGROUND OF THE INVENTION

The invention relates to cancer therapy.

Despite advances in the identification of chemotherapeutic agents for inhibiting the growth of cancer cell, cancer remains a formidable disease with a high mortality rate. A significant problem of chemotherapeutic agents is low specificity. Many anticancer agents do not adequately distinguish normal cells from cancer cells. As a result, they often carry undesirable serious side effects.

SUMMARY OF THE INVENTION

The invention provides a method of inhibiting tumor growth in a mammal with few or no deleterious side effects. The method is carried out by administering to the mammal composition containing an active methylol-containing compound. The compound is administered to directly contact a tumor cell at a dose sufficient to induce cell death by apoptosis. Preferably the compound is administered in a manner and at a dose which preferentially induces apoptotic death compared to necrotic death. By "methylol containing compound" is meant a compound which contains or is capable of producing a methylol molecule in an aqueous environment. An aqueous environment includes conditions encountered following administration to a mammal, i.e., under physiological conditions. A molecule of taurolidine produces three methylol molecules, whereas a molecule of taurultam produces one methylol species.

A method of treating an autologous tumor, e.g., a tumor of the central nervous system (CNS), is carried out by administering to a mammal, e.g., a human patient, a methylol-containing compound. The compound is administered systemically, e.g., orally or intravenously, or infused directly into the brain or cerebrospinal fluid. An erodible or resorbable solid matrix such as a wafer or sponge is implanted directly into brain tissue. Preferably, the tumor is a glioma, astrocytoma, neuroblastoma, or CNS metastasis from a non-CNS primary tumor.

The methylol-containing compound is characterized as having a R—CH$_2$—OH group in which R is an alkyl, aryl or hetero group. The invention also includes compounds capable of producing or being converted into a compound containing a R—CH$_2$—OH structure. Preferably the compound is taurolidine, taurultam, or a derivative thereof (Tables 1, 2). R is an alkyl, aryl, hydrogen or hetero group or atom.

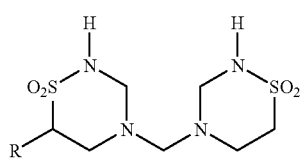

Taurolidine

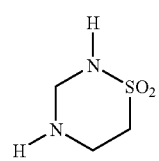

Taurultam

Alternatively, the compound is a taurinamide derivative, e.g., a compound shown in Table 3; or a urea derivative, e.g., a compound shown in Table 4.

TABLE 1

Taurolidine Derivatives

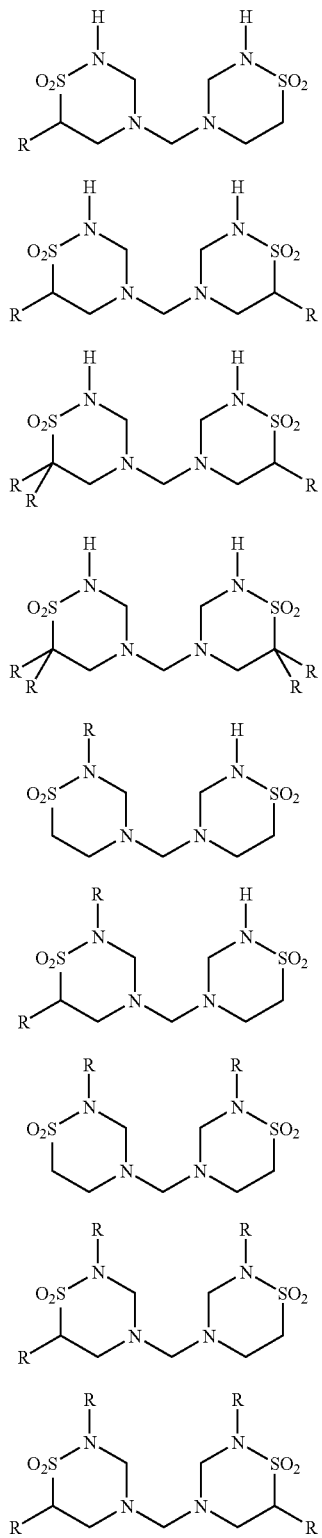

TABLE 1-continued

Taurolidine Derivatives

[Chemical structures of taurolidine derivatives]

R = alkyl, aryl, hydrogen, or hetero group or atom

TABLE 2

Taurultam Derivatives

[Chemical structures of taurultam derivatives]

R = alkyl, aryl, hydrogen, or hetero group or atom

TABLE 3

Taurinamide Derivatives $NHSO_2CHCH_2NHCH_2OH$
  |
  R $NHSO_2CCH_2NHCH_2OH$
  |
  R

R
       |
$NHSO_2CHCHNHCH_2OH$
            |
            R

R  R
       | /
$NH_2SO_2CCHNHCH_2OH$
       |
       R

R  R
    | /
$NH_2SO_2CCNHCH_2OH$
    |  \
    R   R

R
       |
$NH_2SO_2CHCHNCH_2OH$
       |  |
       R  R

R
    |
$NH_2SO_2CHCH_2NCH_2OH$

R = alkyl, aryl, hydrogen, or hetero group or atom

TABLE 4

Urea Derivatives $R—NHCONHCH_2OH$    $R—NHCONCH_2OH$
                              |
                              R R = alkyl, aryl, hydrogen, or hetero group or atom Other methylol-containing compounds suitable for inducing apoptotic death of cancer cells include but are not limited to 1,3-dimethylol-5,5-dimethylhydantoin, hexamethylene tetramine, or noxythiolin.

By derivative of taurolidine or taurultam is meant a sulfonamide compound which possesses at least 10% of the neoplastic activity of taurolidine or taurultam, respectively. A sulfonamide compound is one having a $R_2N—SO_2R'$ formula. Derivatives of the compounds described herein may differ structurally from a reference compound, e.g., taurolidine or taurultam, but preferably retain at least 50% of the biological activity, e.g., induction of apoptotic cell death, of the reference compound. Preferably, a derivative has at least 75%, 85%, 95%, 99% or 100% of the biological activity of the reference compound. In some cases, the biological activity of the derivative may exceed the level of activity of the reference compound. Derivatives may also possess characteristics or activities not possessed by the reference compound. For example, a derivative may have reduced toxicity, prolonged clinical half-life, or improved ability to cross the blood-brain barrier.

The methylol-containing compound is administered alone or in combination with a second antineoplastic agent. Preferably, the coadministered agent kills tumors cells by a mechanism other than apoptosis. For example, an antimetabolite, a purine or pyrimidine analogue, an alkylating agent, crosslinking agent (e.g., a platinum compound), and intercalating agent, and/or an antibiotic is administered in a combination therapy regimen. The coadministered drug is given before, after, or simultaneously with the methylol-containing agent. For example, taurolidine enhances the effect of another drug or radiation therapy by increasing the number of certain types of cancer cells in "S" phase. An advantage of such a combination therapy approach is that a lower concentration of the second neoplastic is required to achieve tumor cell killing.

The invention also includes treating a drug resistant tumor, e.g., a multiple drug resistant (MDR) tumor in a mammal by administering to the mammal a methylol-containing compound. The tumor to be treated is a carcinoma or sarcoma. The drug resistant tumor is selected from the group consisting of a solid tumor, a non-solid tumor, and a lymphoma. For example, the drug resistant tumor is a breast cancer, ovarian cancer, colon cancer, prostate cancer, pancreatic cancer, CNS cancer, liver cancer, lung cancer, urinary bladder cancer, lymphoma, leukemia, or sarcoma.

Any neoplastic cell can be treated using the methods described herein. Preferably, the methylol-containing compound, e.g., taurolidine, taurultam, or a derivative thereof, is administered in a manner which allows direct contact of the surface of the tumor cell with the methylol-containing compound. The compound itself or a methylol molecule produced by the compound binds to a component, e.g., a cell surface polypeptide ligand or other cell surface moiety to initiate an intracellular signal transduction cascade culminating with cell death by apoptosis. Tumors to be treated include but are not limited to leukemia, lymphoma, breast cancer, ovarian cancer, colon cancer, prostate cancer, pancreatic cancer, CNS cancer, liver cancer, urinary bladder cancer, sarcoma, and melanoma. For example, bladder cancer is treated by inflating the bladder with a solution containing a methylol-containing compound, and skin cancers such as basal cell carcinomas or squamous cell carcinomas are treated by applying a methylol-containing compound formulated as a film, cream, or ointment, directly to the affected skin area. For treatment of primary liver cancers or liver metastases, the compounds are infused into the hepatic artery, portal vein, or other blood vessel of the liver. Alternatively, slow release of the compound to any tissue is accomplished by implanting a drug loaded matrix in direct contact or adjacent to the tumor site.

To purge a mixed population of cells, e.g., a patient derived sample of bone marrow cells or peripheral blood cells, of contaminating cancer cells, the bone marrow cells or peripheral blood cells are cultured in the presence of a methylol-containing compound such as taurolidine or taurultam. The ex vivo treated cells are then washed and expanded in culture or infused into a mammalian recipient, e.g., the individual from which the cells were derived or another mammalian recipient. The number of tumor cells in the mixed population is reduced by at least one, preferably at least two, more preferably at least three, more preferably at least four, and most preferably at least five log units, after treatment.

The methylol-containing compounds are formulated for administration to directly contact cancer cells, e.g., in the form of an aqueous solution. Formulations include a therapeutic film-forming composition containing or coated with a methylol-containing compound as well as ointments, pastes, sprays, patches, creams, gels, sponges, and foams.

Other features and advantages of the invention will be apparent from the following detailed description and from the claims.

DETAILED DESCRIPTION

Figure 1:
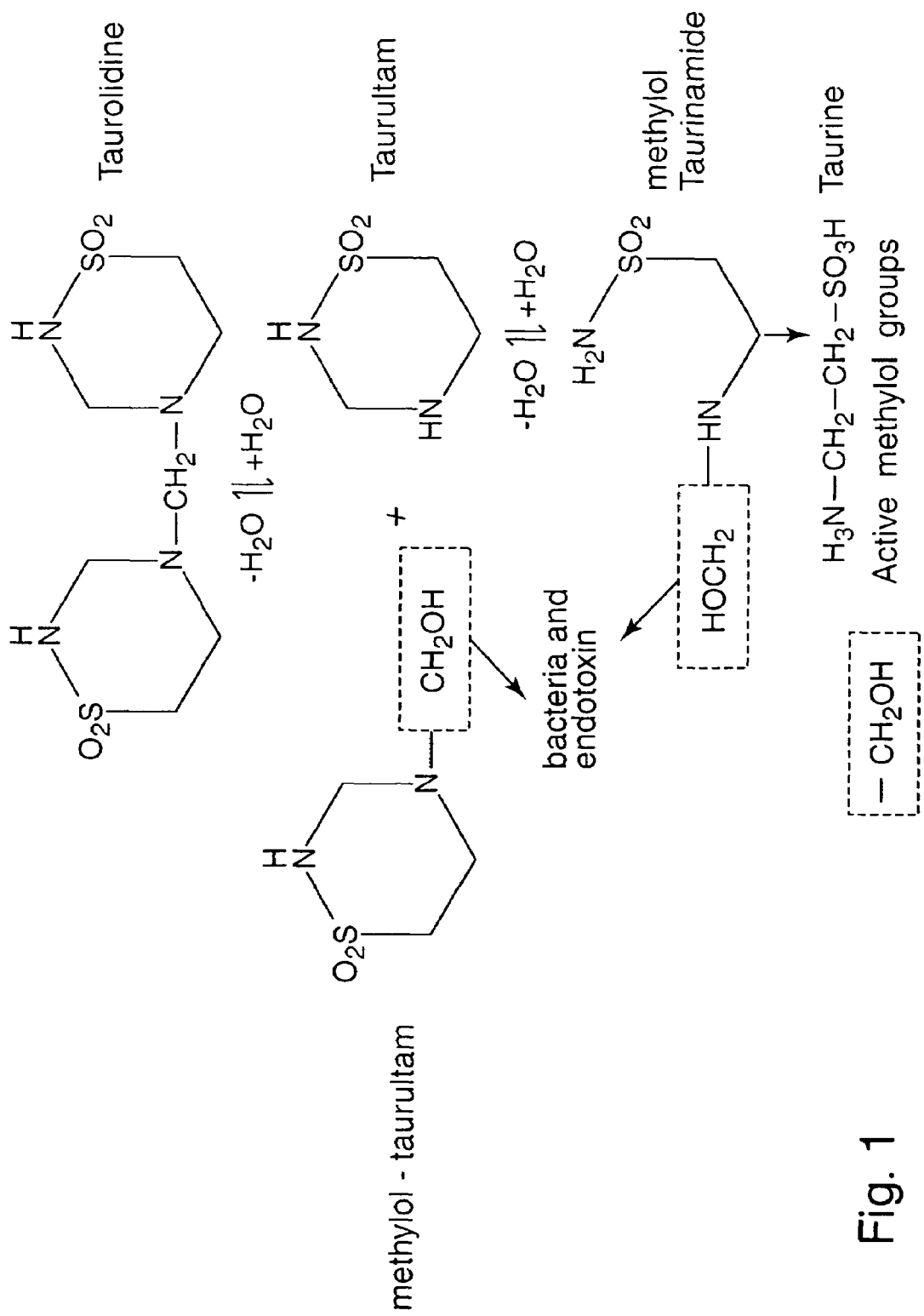
FIG. 1 is a diagram of the structure of Taurolidine and its major breakdown products or metabolites (taurultam, taurinamide and taurine). Upon breakdown, each molecule of Taurolidine generates 3 methylol containing moieties implicated the antibiotic and anti-endotoxin activities of taurolidine.

Taurolidine and taurultam were found to be safe and effective antineoplastic agents which preferentially induce apoptotic death in cancer cells. Compounds which function as methylol donors can be used to induce apoptotic death of tumor cells. A functional group (methylol) can be incorporated into a variety of compounds which then act as methylol carriers.

Methylol-containing Compounds

Taurolidine was found to be selectively toxic to cancer cells without killing normal (i.e., noncancerous) cells. Upon administration to a subject, taurolidine, in an aqueous environment exists in equilibrium with several methylol-containing or producing species. Hydrolysis of taurolidine in vivo leads to methylol taurultam and taurultam in equilibrium. Administration of taurolidine to a mammal also produces N-methylol-taurinamide and taurultam. The active antineoplastic agent is a methylol-containing compound.

Upon hydrolysis of taurolidine, in aqueous solutions, one methylol group is formed from the bridgehead methylene between the rings as taurultam-methylol. Taurultam is further transferred via methylol taurinamide to taurine. Thus, three active methylol molecules are produced per molecule of taurolidine following administration to a mammal. One active methylol molecule is produced per molecule of taurultam, and two active methylol molecules are produced from taurultam-methylol. Each methylol group has high affinity for and binds selectively to a moiety on the surface of a cancer cell (e.g., a phosphatidyl serine receptor) and induces apoptosis in that cell, which in turn leads to cytotoxicity. Cellular internalization of a methylol-containing compound or a methylol molecule may not be necessary for induction of apoptotic death of a cancer cell.

Cytotoxicity or cell death may occur by either necrosis or apoptosis. Necrosis, which is not genetically controlled, is usually the result of physical or chemical injury. Apoptosis is genetically controlled and is a cellular response to a specific stimuli, e.g., a cell surface-generated signal. Necrosis involves the destruction of cytoplasmic organelles and a loss of plasma membrane integrity, whereas cells undergoing apoptosis exhibit cell shrinkage, membrane blebbing, chromatin condensation and fragmentation. After the DNA damage in the caspase enzyme pathway, there are a series of events which occur that involve calcium activation and calpain enzymes which further leads to other cellular changes and regulation of cytoplasmic enzymes.

A major difference between necrosis and apoptosis in vivo is the elimination of the apoptotic cell before an inflammatory response is mounted. In contrast to apoptosis of cells, necrosis of cells causes inflammation. Thus, induction of cytotoxicity of cancer cells by apoptosis offers considerable advantages over induction of cell death by convention chemotherapeutic agents because apoptotic death is associated with minimal damage to surrounding cells or tissue. Unlike many conventional chemotherapeutic agents methylol-containing agents such as taurolidine or taurultam administered according to the invention are cytotoxic agents which induce apoptosis of cancer cells (but not normal noncancerous cells) to safely reduce the tumor burden in a mammal suffering from cancer.

Functional Characterization of Taurolidine

Taurolidine (Taurolin™) is chemically identified as Bis-(1, 1-dioxoperhydro-1,2,4-thiadiazinyl-4)methane (FIG. 1). It is a relatively small dimeric molecule with a molecular weight of 284 (Knight et al., 1983, J. Pharm. Sci 72:705-707)). Early assessment of its antibiotic activity revealed that it possessed bactericidal activity against a broad spectrum of aerobic and anaerobic bacterial strains. The minimum concentration required to inhibit bacterial cell growth (MIC) ranged from 0.01 to 1 mg/ml, depending on the bacterial strain evaluated. Early studies also revealed that Taurolidine possessed activity against clinically relevant fungi. The concentration required to exert antifungal activity is approximately equivalent to that required to produce its antibacterial activity.

The antibiotic activity of Taurolidine depends upon a chemical reaction secondary to the generation of active methylol groups formed upon the decomposition of the parent Taurolidine molecule (FIG. 1). Biochemical and morphological studies revealed that Taurolidine-derived methylol group containing moieties appeared to react with bacterial cell wall components. The result of this chemical reaction is that exposure to this agent significantly inhibits the ability of microorganisms to adhere to biological surfaces, such as epithelial cells. Exposure to Taurolidine disrupted the structure, and reduced the number, of bacterial cell fimbriae, apparently a reflection of the agglutination of these structures. Modification of these surface structures is thought to be responsible for the ability of Taurolidine to disrupt bacterial cell adhesion. In addition to this direct effect on bacterial cell wall components, Taurolidine also possesses anti-endotoxin activity by reducing tumor necrosis factor alpha (TNF-α) synthesis and activity. Taurolidine also reduces the extent and severity of postoperative peritoneal adhesions and has been administered clinically, by lavage, after abdominal surgery to reduce post-operative infections and adhesions as well as to treat peritonitis.

Taurolidine is a synthetic broad-spectrum antibiotic that also possesses antifungal activity. Mechanistically, it reacts with bacterial cell membrane components to prevent the adhesion of bacterial cells to epithelial cell surfaces. Reflecting the key role of cell adhesion in the growth and development of human solid tumors, studies were initiated to assess the cytotoxic activity of this agent against the growth of a panel consisting of 12 selected human and murine tumor cell lines. Assessment of the growth inhibitory activity of a 3 d Taurolidine exposure revealed that this agent inhibited the growth of all cell lines evaluated with $IC_{50}$s ranging from 9.6-34.2 μM. Studies to identity the underlying mechanism(s) responsible for this effect were conducted in NIH-3T3 murine fibroblasts and the PA-1 and SKOV-3 human ovarian tumor cell lines. Initial studies assessed the effect of a 48 h exposure to Taurolidine on cell cycle distribution. The results of this analysis revealed that while Taurolidine had little effect on the cell cycle in PA-1 cells, in SKOV-3 cells it reduced the percentage of cells in the $G_0/G_1$-phase and increased the percentage of cells in both S and $G_2/M$. In these human tumor cell lines, Taurolidine exposure significantly increased DNA debris in the sub-$G_0/G_1$ region, an effect consistent with an induction of apoptosis. In contrast, in NIH-3T3 cells, Taurolidine increased the percentage of cells in S-phase, decreased the percentage of cells in $G_0/G_1$, and did not increase DNA debris in sub-$G_0/G_1$ region. Further studies of the relationship between Taurolidine exposure and tumor cell apoptosis assessed phosphotidylserine externalization following a 24 h exposure to Taurolidine, using Annexin-V binding as a cell surface marker. These studies revealed that Taurolidine increased the percentage of Annexin-V positive cells by 4- and 3-fold in PA-1 and SKOV-3 cells, respectively. In contrast, in NIH-3T3 cells, Taurolidine exposure slightly increased (~5%) Annexin-V binding. Complementary studies determined if a 48 h exposure to either 50 or 100 μM Taurolidine affected PARP cleavage in these cell models and revealed that Taurolidine induced PARP cleavage in both PA-1 and SKOV-3 cells. In total, these in vitro results reveal that Taurolidine possesses tumor cell cytotoxic activity that correlates with its ability to specifically induce apoptosis. Finally, murine-based studies were conducted to assess the antineoplastic activity of this agent. Initial studies assessed the toxicity of 3 consecutive daily i.p. bolus injections of Taurolidine, at doses ranging from 5 mg/inj/mouse-30 mg/inj/mouse. The 20 mg/inj dose produced ~10% mortality and was identified as the MTD in this model. Administration of this Taurolidine regimen to nude mice bearing i.p. human ovarian tumor xenografts resulted in a significant inhibition of both tumor formation and growth.

The invention is based on the discovery that, in addition to the activities discussed above, taurolidine selectively and reliably inhibits tumor cell growth and selectively kills tumor cells by inducing apoptosis. Taurolidine has now been found to kill at least 28 different human tumor cell lines including ovarian, breast, brain, colon, prostate, urinary bladder and lung tumors, as well as melanomas, mesotheliomas, laryngeal carcinomas, leukemias, and lymphomas. In addition, multiple-drug resistant glioma clls and myelodysplastic syndrome cells (a precancerous cell type) were killed by taurolidine. Inhibition of tumor growth and induction of tumor cell death occur at taurolidine concentrations significantly lower than those required for antibiotic activity. For example, for antineoplastic applications, taurolidine is administered at a dose that is at least 10% less, preferably at least 20% less, more preferably at least 50% less, and up to one log unit less than the dose required for antibacterial or antiadhesive activity.

Taurolidine is toxic to tumor cells (but not normal non-tumor cells) regardless of the tumor origin. Apoptosis of tumor cells s induced after an incubation with Taurolidine for as little as one hour in culture.

Taurolidine and metabolites thereof are also useful in combination therapy. The data indicate that taurolidine is useful to enhance the cytotoxicity of other chemotherapeutic agents and/or radiation therapy by inducing certain types of cancer cells to enter "S" phase.

Taurolidine and Angiogenesis

Patients with metastatic colon cancer were treated with taurolidine and several factors controlling angiogenesis were measured. Four factors controlling the growth of blood vessels (tissue necrosis factor (TNF); interleukins 1, 6, and 10; vascular endothelial growth factor (VEGF); and tumor growth factor-β (TGF)) were found to be decreased in taurolidine-treated subjects compared to subjects receiving placebo. These data indicate that taurolidine has anti-angiogenesis activity and is useful to inhibit tumor growth by decreasing new blood vessel formation.

Therapeutic Administration

An effective amount of a methylol-containing compound is preferably from about 0.1 mg/kg to about 150 mg/kg. However, due to the low toxicity of taurolidine and taurultam compounds, higher doses may be administered without deleterious side effects. A dose effective to induce apoptosis of cancer cells is an order of magnitude less than doses administered for antiseptic, antibacterial, antitoxic, or anti-adhesion purposes. An apoptotic close of taurolidine or taurultam effective to induce apoptosis (e.g. 0.5 µg/dl) is also significantly less than doses previously suggested (e.g., 150-450 mg/kg) as potentially being useful in the treatment of certain cancers. Effective doses vary, as recognized by those skilled in the art, depending on route of administration, excipient usage, and coadministration with other therapeutic treatments including use of other antitumor agents (e.g., an antimetabolite, a purine or pyrimidine analogue, an alkylating agent crosslinking agent, intercalating agent, or an antibiotic,) and radiation therapy.

A therapeutic regimen is carried out by identifying a mammal. e.g., a human patient suffering from (or at risk of developing) a cancer or metastases using standard methods. For example, taurolidine or taurultam is administered to an individual diagnosed with a cancer (e.g., acute myeloid leukemia) or an individual diagnosed with a precancerous condition (e.g., myelodysplasia which may progress to acute myeloid leukemia). The pharmaceutical compound is to administered to such an individual using methods known in the art. Preferably, the compound is administered orally, topically or parenterally, e.g., subcutaneously, intraperitoneally, intramuscularly, and intravenously. For example, ovarian cancer may be treated by intraperitoneal lavage using a pharmaceutically-acceptable solution of taurolidine or taurultam. The compound is administered prophylactically, after the detection of a recurring tumor, or at the time of surgery. The compound may be formulated as a component of a cocktail of chemotherapeutic drugs) to treat a primary ovarian cancer or to prevent recurring tumors. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

A methylol-containing compound is formulated into compositions for other routes of administration utilizing conventional methods. For example, it can be formulated in a capsule or a tablet for oral administration. Capsules may contain any standard pharmaceutically acceptable materials such as gelatin or cellulose. Tablets may be formulated in accordance with conventional procedures by compressing mixtures of a methylol-containing compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, paste, spray, patch, cream, gel, resorbable sponge, or foam. Such formulations are produced using methods well known in the art.

Methylol-containing compounds such as taurolidine or taurultam are effective upon direct contact of the compound with the cancer cell. Accordingly, the compound is administered topically. For example, to treat urinary bladder carcinoma, the compound is administered to the bladder using methods shell known in the art, e.g., using a catheter to inflate the bladder with a solution containing the methylol-containing compound for at least ten minutes. For example, the bladder is instilled with a solution of taurolidine or taurultam, and the solution allowed to remain in the bladder for 30 minutes to 2 hours. For treatment of skin malignancies such as basal cell carcinomas, a cream or ointment is applied to the area of skin affected by the tumor. Tumor cells in the liver (e.g., a primary tumor or liver metastases originating from primary tumor elsewhere in the body such as the colon or breast) are treated by infusing into the liver vasculature a solution containing a methylol-containing agent. Alternatively, the compounds are administered by implanting (either directly into an organ such as the liver or subcutaneously) a solid or resorbable matrix which slowly releases the compound into adjacent and surrounding tissues of the subject. Implantation of a drug-loaded matrix directly into the liver effectively destroys tumor cells in the liver, while healthy liver tissue rapidly detoxifies any residual chemotherapeutic agent.

For treatment of cancers of the CNS such as glioblastomas, the compound is systemically administered or locally administered directly into CNS tissue. The compound is administered intravenously or intrathecally (i.e., by direct infusion into the cerebrospinal fluid). For local administration, a compound-impregnated wafer or resorbable sponge is placed in direct contact with CNS tissue. A biodegradable polymer implant such as a GLIADEL™ wafer is placed at the tumor site, e.g., after surgical removal of a tumor mass. A biodegradable polymer such as a polyanhydride matrix, e.g., a copolymer of poly (carboxy phenoxy propane):sebacic acid in a 20:80 molar ratio, is mixed with a therapeutic agent, e.g., taurolidine or taurultam and shaped into a desired form. Alternatively, an aqueous solution or microsphere formulation of the therapeutic agent is sprayed onto the surface of the wafer prior to implantation. The compound or mixture of compounds is slowly released in vivo by diffusion of the drug from the wafer and erosion of the polymer matrix. A methylol-containing compound such as taurolidine or taurultam may be coadministered with other chemotherapeutic agents such as carmustine (BCNU).

Alternatively, the compound is infused into the brain or cerebrospinal fluid using known methods. For example, a burr hole ring with a catheter for use as an injection port is positioned to engage the skull at a burr hole drilled into the skull. A fluid reservoir connected to the catheter is accessed by a needle or stylet inserted through a septum positioned over the top of the burr hole ring. A catheter assembly (e.g., an assembly described in U.S. Pat. No. 5,954,687) provides a fluid flow path suitable for the transfer of fluids to or from selected location at, near or within the brain to allow administration of the drug over a period of time.

The compounds are also used to purge a sample of bone marrow cells of cancer cells which may contaminate the sample. Bone marrow cells are derived from a mammalian donor using standard methods. The cells are treated by contacting them with a methylol-containing compound in vitro to eliminate contaminating tumor cells. After washing the treated cells, the bone marrow cell preparation is administered to a mammalian recipient to reconstitute the immune system of the recipient.

Similarly, a population of peripheral blood mononuclear cells is purged of tumor cells. Peripheral blood may be used as a source of stem cells, e.g., hematopoetic stem cells, for repopulating the immune system of a cancer patient following chemotherapy or radiation therapy. In some cases (e.g., patients with a myeloma or breast cancer), using peripheral blood as a source of stem cells is preferable to using bone marrow because the peripheral blood may be less contaminated with tumor cells. Peripheral blood mononuclear cells are obtained from an individual using standard methods, e.g., venipuncture or plasmapheresis. The cells are treated with a methylol-containing compound such as taurolidine, taurultam, or a derivative thereof, in vitro to kill contaminating tumor cells. The cells are washed and infused into a recipient individual. Optionally, the cells are cultured to expand a desired cell type.

Cytotoxicity of Methylol-containing Compounds

The cytotoxic activity of taurolidine was evaluated in vitro against the growth of a variety of human cancer cell lines as well as "normal" NIH 3T3 fibroblasts and found to induce apoptotic cytotoxicity. The neoplastic cell lines used in the survey were standard tumor cell lines, e.g., PA1 human ovarian cell line. SKOV3 human ovarian cell line, HT29 human colon tumor cell line. DU145 human prostate tumor cell line. U251 human glioblastoma cell line, U251-MDR human glioblastoma cell line transfected with DNA encoding MDR. T98G human glioblastoma cell line. SP-1 human leukemia cell line, and Daudi human leukemia cell line.

The data indicated that taurolidine inhibited human cancer cell growth. Surprisingly, the concentration of taurolidine required to inhibit tumor cell growth after a 3-day exposure to the compound ($IC_{50}$) was approximately 12.5 μM-50 μM. This concentration is at least 1000-fold lower than concentrations used to inhibit bacterial cell growth.

Taurolidine and cancer cells were added to flasks simultaneously, and cell growth was assessed 3 days later. Parallel studies were carried out to assess whether disruption of cell adhesion played a role in the cytotoxic activity. Assays were carried out to assess the ability of taurolidine to inhibit the growth of human ovarian tumor cells after they were established and growing in vitro as discrete colonies. The data revealed that a 24-hour exposure to 50 μM taurolidine produced a significant cytotoxic effect against the growth of established tumor cells. The data indicated that the cytotoxic/cytostatic activity of taurolidine is not due to inhibition of tumor cell adhesion.

The mechanism by which taurolidine produces cytoxicity was evaluated. Cell cycle kinetics and cell cycle distribution of tumor cells were examined after a 24-hour exposure to taurolidine. The results revealed that in both PA1 and 3T3 cells, taurolidine exposure disrupted cell cycle kinetics and significantly reduced the percentage of cells in both the S- and G2/M-phases. Exposure of PA1 human ovarian cells to this regimen of taurolidine also induced a high degree of DNA fragmentation indicating the induction of apoptosis. This DNA fragmentation was not observed in normal 3T3 cells.

To further evaluate the possibility that exposure to 50 μM taurolidine was capable of specifically inducing apoptosis in human ovarian tumor cells but not normal fibroblasts, studies were undertaken to evaluate DNA fragmentation as a function of taurolidine exposure by using agarose-gel electrophoresis. The results confirmed that, in ovarian tumor cells, exposure to taurolidine resulted in overt DNA fragmentation which was not apparent in 3T3 cells exposed to an identical taurolidine regimen.

The cytotoxic activity of taurultam was evaluated in vitro using the same human cancer cell lines as described above. The data indicated that taurultam induced apoptotic death of cancer cells but not normal control cells in the same manner as taurolidine. The cytotoxic activity of taurultam was approximately 75% of the activity observed with taurolidine. These data confirm that a class of compounds defined by the ability to release a methylol moiety exerts a potent and specific cytotoxic effect on cancer cells. The data also indicate that the cytotoxic effect is directly proportionate to the number of methylol molecules liberated per molecule of methylol-containing compound Apoptotic death is distinguished from death by other mechanisms using methods known in the art. Another early reflection of the induction of apoptosis is the cleavage of the protein poly (ADP-ribose) polymerase (PARP) by cellular caspases. Western-blot based studies were carried out to determine if exposure to taurolidine resulted in PARP cleavage. The results revealed that PARP cleavage was not evident in 3T3 cells when exposure to the same taurolidine regimen. Apoptosis is also detected using known methods such as determination of caspase activation, bax/bcl12 ratios and fas and fas-I interactions. Other methods of distinguishing between apoptosis and necrosis (e.g., a fluorescence-based method described in U.S. Pat. No. 5,976,822) are used to determine the mechanism of death or the dose at which a methylol-containing compound induces apoptosis compared to necrosis.

The antitumor activity of a compound is also evaluated using a standard MTS colorimetric assay. Results obtained with various types of tumor cells (primary cells or cell lines) are compared with those obtained by using normal cells. Viability of the cells in each cell line is estimated by measuring the cellular conversion of a tetrazolium salt after incubating the cells in a solution containing a test compound in a 96 well plate. $IC_{50}$ values obtained using the identical test compound on normal cells and cells of a particular tumor cell line are compared and their ratio ($IC_{50}$ normal cell/$IC_{50}$ cancer cell) indicates the cancer selectivity of the test compound. An increase in the $IC_{50}$ normal cell/$IC_{50}$ cancer cell ratio reflects a higher selectivity of the test compound to kill the cancer cell.

Antitumor activity of a compound is also evaluated in vivo using, e.g., a tumor xenograft regression assay. For example animals bearing established tumors are treated with a test compound for a three-week period. The growth of the tumors and the general health of the animal are monitored during the three-week treatment and for two more weeks after treatment to determine if tumor regrowth occurs. The antineoplastic activity of taurolidine is determined in athymic (nude) mice bearing advanced and/or metastatic xenografts. Single and multiple dose regimens of taurolidine are evaluated in athymic (nude) mice. Upon identification of dose regiments, antineoplastic activity is assessed in athymic (nude) mice bearing xenografts of human cancer cells, e.g., ovarian, prostate, colon, pancreatic, breast and glioma tumors.

Treatment of Leukemias and Lymphomas

The compounds described herein are particularly effective in killing tumor cells which are not anchorage-dependent such as leukemias or lymphomas. The cytotoxic effect is not due to inhibition of cell adhesion.

Two different non-anchorage-dependent tumor cell lines (a human Burkitt's lymphoma cell line, and a Daudi cell line), and precancerous cell line (a human myelodysplastic cell line) were grown in suspension culture. After exposing the tumor cells to 10-20 μM of taurolidine for 72 hours, 50% of the cells died. Similar results were observed after exposure of the myelodysplastic cells to taurolidine. These results indicate that taurolidine is useful to treat non-anchorage-dependent tumor cell types such as lymphomas or leukemias. The results also indicate that precancerous cells such as myelodysplastic cells are effectively killed by the compounds described herein and that individuals diagnosed with myelodysplasia (which may develop into an acute myeloid leukemia) may be effectively treated using taurolidine or other methylol-containing compounds described herein.

Treatment of Ovarian Cancer

Over 80% of patients diagnosed with ovarian cancer experience recurrent tumors after therapeutic intervention for the primary tumor. Even a 5% response rate, e.g., a 5% reduction in tumor growth, would confer a clinical benefit. Response rate is defined as a reduction in tumor size or in the number of metastatic foci. For example, a reduction in tumor size is determined by detecting a decrease in the size of the largest neoplastic lesion, e.g., by sonogram or by measurement using a caliper.

A standard mouse model of ovarian cancer was used to study the effect of taurolidine on recurrent ovarian cancer. Holland Sprague-Dawley mice were injected with $5 \times 10^6$ tumor cells (e.g., SKOV3 human ovarian tumor cell line) to mimic a condition of advanced ovarian cancer. Taurolidine was administered by intraperitoneal lavage 5 days later. Taurolidine was administered 3 times a day for 4 days at a dose of 30 mg/day. At least a 75-80% reduction in tumor foci was observed. These data indicate that administration of taurolidine reduces ovarian tumor burden and recurrence of tumors Treatment of Drug Resistant Tumors Taurolidine was found to be particularly effective in killing tumor cells which are refractory to cytotoxicity by other known chemotherapeutic agents. Glioblastoma cells were transfected with a gene encoding multiple drug resistance (MDR). The transfected cells were 100-1000 times resistant to standard chemotherapeutic agents, e.g., adriamycin. Untransfected glioblastoma cells cultured with a standard dose (e.g., 1 μm) of adriamycin were killed, but MDR-transfected glioblastoma cells contacted with 1 μM of the drug were resistant. Significant cytotoxicity of the MDR-transfected glioblastoma cells was observed after contact with a methylol-containing compound (e.g., taurolidine at a dose of 50 μM). These data indicate that methylol-containing compounds such as taurolidine exert their cytotoxic activity via a mechanism that differs from that of standard chemotherapeutic agents. Accordingly, combination therapy in which a methylol-containing compound is administered before, after, or together with another chemotherapeutic agent (e.g., an antimetabolite, a tumor-specific monoclonal antibody, or anti-angiogenic agent) results in improved clinical outcome of patients suffering from a malignant condition characterized by a mixed population of tumor cells (e.g., those which are killed by standard chemotherapeutic agents and those which are MDR).

EXAMPLE 1

Cytotoxic and Mechanistic Evaluation of Antineoplastic Agents

Taurolidine was found to be active at inhibiting the growth of a variety of human tumor cell lines in vitro. PA-1 and SKOV-3 human ovarian tumor cell lines and NIH-3T3 murine fibroblasts were used to determine the mechanism of antitumor activity. The studies revealed that this effect was associated with alterations in DNA structure, cell membrane components, and protein cleavage that were consistent with the induction of apoptosis specifically in tumor cells. Antineoplastic evaluation of Taurolidine in nude mice bearing intraperitoneal xenografts of human ovarian tumors demonstrated that this agent significantly inhibited tumor development and growth in vivo.

To study neoplastic activity, Taurolidine was formulated as 2% solution in 5% Kollidon 17PF. Standard cell culture growth media (e.g., High glucose DMEM, RPMI 1640, McCoy's 5A, and F12K), trypsin, and fetal bovine serum (FBS) were all purchased from GIBCO/Life Technologies (Grand Island, N.Y.). Phosphotidylserine externalization by cells was evaluated using the ApoAlert® Annexin-V/FITC assay kit was purchased from Clontech (Palo Alto, Calif.). Reagents for SDS-PAGE were purchased from BioRad Laboratories (Richmond, Calif.). A murine monoclonal antibody (clone C-2-10) to human PARP was purchased from Zymed Laboratories (San Francisco, Calif.). All other chemicals were purchased from Sigma (St. Louis, Mo.).

Studies to assess the cytotoxic activity of Taurolidine were carried out using a panel of human solid tumor cell lines as well as in NIH-3T3 murine fibroblasts. Included in the tumor cell line panel were ovarian tumor cells (PA-1 and SKOV-3), colon tumor cells (HCT-8, HCT-15 and HT-29), lung tumor cells (H-157, A-549 and H-596), prostate tumor cells (DU-145), glioma cells(U-251), and melanoma (MNT-1). The murine melanoma B16F10 cell line was also tested. These cell lines readily available, e.g., from the American Type Culture Collection (ATCC). Cells were cultured in appropriate growth medium at 37° C. in a humidified incubator in an atmosphere of 5% $CO_2$. Under these growth conditions, the doubling time of all cell lines was 20-28 h.

Studies to assess in vivo toxicity and therapeutic effectiveness were carried out in 6-12 week old female homozygous athymic (Hsd:athymic nude nu/nu) mice obtained from Harlan (Indianapolis, Ind.).

To evaluate inhibition of cell growth, subconfluent cultures of appropriate cell lines were harvested by trypsinization and resuspended in media at a cell density of $1-5 \times 10^4$ cells/ml. One ml of this cell suspension was added to each well of a 12 well cell culture plate that contained 3 ml of appropriate media plus serum. Twenty-four hours later, Taurolidine was added to each well, in a volume of 40 μl, to achieve a final concentration of 0.1-200 μM. Control wells received 40 μl of 5% Kollidon 17PF alone. Seventy-two hours later, all cells were harvested by trypsinization and cell number determined electronically using a Coulter Model Z1 particle counter (Coulter Corp., Miami, Fla.) to assess cell growth inhibition. Each experiment was performed in duplicate and repeated a minimum of three times.

For flow cytometry studies, $1 \times 10^6$ PA-1, SKOV-3, or NIH-3T3 cells were incubated for 24 h in appropriate media containing serum. Twenty-four hours later, Taurolidine was added in a volume of 40 μl to achieve a final concentration of 25, 50, or 100 μM. Control cultures for each cell line were incubated in media containing 40 μl of 5% Kollidon 17PF alone. Forty-eight hours later, all cells were harvested by trypsinization and prepared for cytofluorometric analysis by standard methods. For example, harvested cells were resuspended in ice cold phosphate-buffered saline at a final cell density of $2 \times 10^6$ cells/ml. The cells then were stained for 30 min at room temperature in the dark with a solution of 0.05 mg/ml propidium iodide, 0.6% Igepal, and 1% sodium citrate. Flow cytometry was performed by FACScan (Becton Dickinson, Plymouth, England) using the ModFit LT program (Becton Dickinson). Statistical analysis was performed with the Kruskal Wallis non-parametric ANOVA test followed by Dunn's multiple comparisons test using Instat.

Cell membrane phosphotidylserine externalization, as a reflection of the potential induction of apoptosis, was assessed by flow cytometry methods using the ApoAlert® Annexin-V/FITC assay kit. Briefly $1 \times 10^6$ cells were incubated for 24 h in tissue culture medium containing serum. Thereafter, Taurolidine was added to achieve a final concentration of 25, 50, or 100 µM. Control cultures received 5% Kollidon 17PF alone. Twenty-four hours later. all cells were harvested by trypsinization. The harvested cells were resuspended in 200 µl of binding buffer and then incubated for 5-15 min in a solution containing 1 µg/ml Annexin-V FITC at room temperature in the dark. The cells were then analyzed to quantitate Annexin-V binding by cytofluorometric techniques that utilized FACScan using the ModFit LT program with statistical analysis as described above.

Western-blot analysis was used to assess of PARP cleavage. Two$\times 10^6$ cells were seeded into separate 75 cm$^2$ tissue culture flasks containing 20 ml of tissue culture media plus serum. Twenty-four hours later, Taurolidine was added at concentrations of 50 µM or 100 µM. Twenty-four hours after the addition of Taurolidine, cells were harvested, cell number determined, and aliquots containing an equal cell number were generated from each exposure condition. Total proteins from whole cell lysates generated from these aliquots were separated by SDS-PAGE and electrotransferred to nitrocellulose filters. Filters were then processed to detect intact PARP protein and cleavage fragments by using the clone C-2-10 mouse monoclonal anti-PARP antibody (Zymed Laboratories, San Francisco, Calif.). The resulting protein-antibody complexes were visualized by standard chemiluminescence techniques.

To evaluate Taurolidine-induced toxicity, mice were divided into groups of 5-8 animals. Thereafter, all mice were weighed and therapy, consisting of a single i.p. bolus injection of Taurolidine on 3 consecutive days, was initiated. The Taurolidine doses evaluated were 5, 10, 15, 20, 25, and 30 mg/mouse/injection and, except for the 25 (1.25 ml) and 30 mg/mouse (1.5 ml) injections, were administered in a volume of 1 ml. Taurolidine for injection was diluted from the 2% Taurolidine solution by the addition of 5% Kollidon 17PF. Control animals received 1 ml injections of 5% Kollidon 17PF alone. Animals were examined daily and body weight recorded twice weekly. A reduction in body weight of greater than 10% was considered significant. The maximally tolerated dose (MTD) was considered to be the dose which produced ~10% mortality.

To evaluate therapeutic effectiveness, mice received a single intraperitoneal injection of $5 \times 10^6$ SKOV-3 cells in a volume of 0.5 ml. Immediately thereafter, mice were randomly divided into treatment groups of 7 animals. Taurolidine therapy, consisting of a single i.p. bolus injection of 20 mg of Taurolidine on 3 consecutive days, was initiated either immediately following tumor cell inoculation or at selected time intervals after tumor cell inoculation ($\leq 5$ d). Control animals received 1 ml injections of 5% Kollidon 17PF alone. Animals were examined daily and body weight recorded twice weekly. Fourteen days following the last Taurolidine injection, mice in all groups were sacrificed by $CO_2$ asphyxiation, all i.p. tumor foci removed and tumor weighed determined. The mean tumor weight for each treatment group was calculated and statistical analysis of differences in the mean tumor weight between treatment groups employed the Student's t-test, p-values of $\leq 0.05$ were considered significant.

Taurolidine Inhibits Tumor Cell Growth

The ability of Taurolidine to inhibit cell growth was assessed in a panel of human and murine neoplastic cell lines comprised of 13 different lines representing 6 different tumor types. The results of this survey revealed that a 3 d exposure to Taurolidine inhibited cell growth in each cell line examined (Table 5).

The $IC_{50}$ of Taurolidine against the growth a selected human and murine neoplastic cell lines was evaluated as follows. Cells were seeded at a density of $1-5 \times 10^4$ cells in each well of a 6 well tissue culture flask. Twenty-four hours later, Taurolidine was added at concentrations ranging from 1-100 µM. After three days, cells were harvested by trypsinization and cell number determined electronically. Cell growth inhibition was determined by comparison to non-Taurolidine exposed control cultures. The $IC_{50}$ was calculated as the concentration required to inhibit cell number by 50%. Each $IC_{50}$ value represents the mean±SE of 4-8 determinations.

TABLE 5

| Tumor site of origin | Cell line | $IC_{50}$ (µM) |
| --- | --- | --- |
| Ovary | PA-1 | 11.4 ± 1.8 |
|  | SKOV-3 | 31.6 ± 7.0 |
| Prostate | DU-145 | 9.8 ± 0.8 |
| Brain | U-251 | 20.1 ± 2.7 |
| Colon | HT-29 | 18.6 ± 1.0 |
|  | HCT-8 | 11.5 ± 0.5 |
|  | HCT-15 | 9.6 ± 3.0 |
| Melanoma | B16-F10 | 30.1 ± 2.6 |
|  | MNT-1 | 22.1 ± 2.1 |
| Lung | H-157 | 32.2 ± 5.6 |
|  | A-549 | 26.8 ± 7.2 |
|  | H-596 | 34.2 |
| Murine fibroblasts | NIH-3T3 | 11.9 ± 1.8 |

Surprisingly, the observed $IC_{50}$s for each cell line were remarkably similar and varied over the relatively narrow range of ~10 µM (PA-1, DU-145, HCT-8, HCT-15, B16F10, and NIH-3T3) to ~35 µM (H-596).

The studies assessed the effect of Taurolidine on tumor cell proliferation. Inhibition of proliferation could reflect either growth arrest or cell death. Therefore, studies were next focused to identify the mechanism(s) by which Taurolidine induced cell growth inhibition. These studies were carried out in the human ovarian tumor cell lines PA-1 and SKOV-3 and in NIH-3T3 murine fibroblasts. Studies employing conventional flow cytometry techniques assessed the effect of a 48 h exposure to Taurolidine on cell cycle distribution in both the PA-1 and SKOV-3 human ovarian tumor cell lines. The results of these studies revealed that exposure to this agent did not induce a consistent pattern of cell cycle alterations.

The effect of a 48 h exposure to selected concentrations of Taurolidine on cell cycle distribution in human ovarian tumor cells (PA-1 and SKOV-3) and murine fibroblasts (NIH-3T3) was carried out as follows. Three$\times 10^5$ cells ere seeded in plastic tissue culture flasks. Twenty-four hours later, Taurolidine was added to achieve final concentrations of 25 µM, 50 µM or 100 µM. Control cultures received an appropriate volume of Kollidine-17P. After an additional 48 h. cells were harvested, stained with propidium iodide, and cell cycle distribution assessed using cytofluorometric techniques. Each value represents the percentage of cells in the noted cell cycle phases and is the mean±SEM of three determinations.

TABLE 6

| Cell Line/Drug Exposure | Cell Cycle Distribution, (%) | | |
|---|---|---|---|
| | $G_0G_1$ | S | $G_2/M$ |
| NIH-3T3 | | | |
| 48 h-0 μM Taurolidine | 46.1 ± 9.2 | 45.0 ± 5.9 | 9.0 ± 3.3 |
| 48 h-25 μM Taurolidine | 42.5 ± 9.6 | 44.9 ± 5.6 | 13.0 ± 4.0 |
| 48 h-50 μM Taurolidine | 33.9 ± 10.2 | 44.3 ± 5.9 | 21.8 ± 4.6 |
| 48 h-100 μM Taurolidine | 25.8 ± 1.7 | 63.2 ± 9.8 | 11.0 ± 11.0 |
| PA1 | | | |
| 48 h-0 μM Taurolidine | 29.9 ± 1.5 | 47.7 ± 1.0 | 22.5 ± 0.5 |
| 48 h-25 μM Taurolidine | 28.4 ± 0.5 | 46.8 ± 0.6 | 24.7 ± 0.9 |
| 48 h-50 μM Taurolidine | 23.7 ± 2.2 | 39.5 ± 12.5 | 36.8 ± 12.4 |
| 48 h-100 μM Taurolidine | 28.4 ± 5.6 | 44.5 ± 23.5 | 27.2 ± 17.9 |
| SKOV3 | | | |
| 48 h-0 μM Taurolidine | 46.7 ± 1.3 | 38.8 ± 4.1 | 13.5 ± 3.6 |
| 48 h-25 μM Taurolidine | 45.8 ± 2.7 | 41.9 ± 4.2 | 12.3 ± 3.1 |
| 48 h-50 μM Taurolidine | 30.7 ± 9.4 | 45.5 ± 12.4 | 30.3 ± 10.5 |
| 48 h-100 μM Taurolidine | 19.9 ± 6.1 | 54.2 ± 8.6 | 25.9 ± 7.8 |

Figure 2:
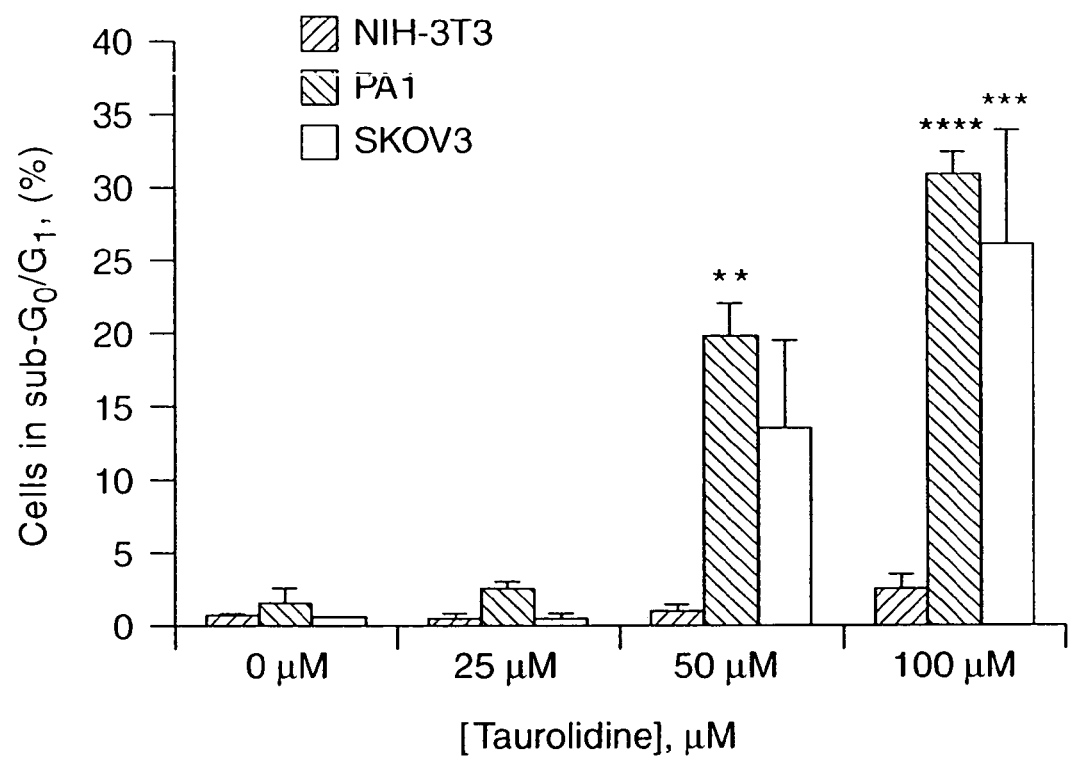
FIG. 2 is a bar graph showing the effect of a 48 h exposure to Taurolidine on the appearance of DNA debris in PA-1, SKOV-3 and NIH-3T3 cells. Three×$10^5$ cells were seeded in plastic tissue culture flasks. Twenty-four hours later, Taurolidine was added to achieve final concentrations of 25 µM, 50 µM or 100 µM. Control cultures received an appropriate volume of Kollidine-17P. After a 48 h period of Taurolidine exposure, cells were harvested and stained with propidium iodide. The percentage of DNA debris in the sub-$G_0/G_1$ region was assessed using cytofluorometric techniques. Each bar represents the mean (±SE) of three determinations. $p \leq 0.01$, *$p \leq 0.001$, **$p \leq 0.0001$

Specifically, in PA-1 cells, a 48 h exposure to up to 100 μM Taurolidine had little effect on cell cycle distribution. Indeed, the percentage of cells in the $G_0/G_1$-, S-, and $G_2$/M-phases were essentially unchanged despite Taurolidine exposure. Alternatively, in SKOV-3 cells, Taurolidine exposure resulted in a concentration-dependent decrease in the percentage of cells in $G_0/G_1$ but increased the percentage of cells in both the S-phase and $G_2$/M. Importantly, in both the PA-1 and SKOV-3 cell lines. Taurolidine exposure also resulted in the appearance of DNA debris in the sub-$G_0G_1$ region, an effect that was Taurolidine concentration-dependent (FIG. 2). Like in the SKOV-3 cell line, exposing NIH-3T3 cells to Taurolidine decreased the percentage of cells in $G_0/G_1$ and increased the percentage of cells in S in a concentration-dependent manner. However, unlike the human ovarian tumor cells assessed. Taurolidine exposure in NIH-3T3 cells did not significantly affect the appearance of DNA debris in the sub-$G_0G_1$ region (FIG. 2).

Figure 3:
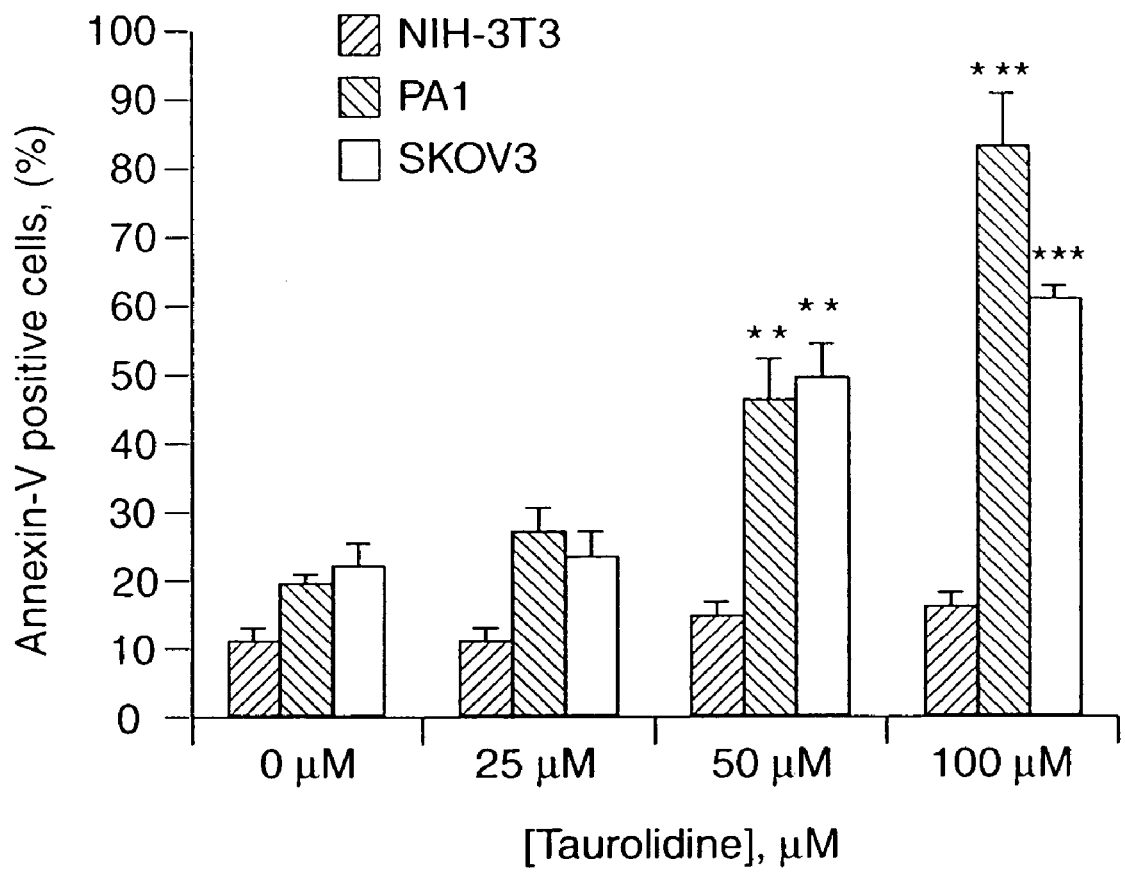
FIG. 3 is a bar graph showing the effect of a 24 h exposure to Taurolidine on membrane phosphotidylserine externalization in PA-1, SKOV-3 and NIH-3T3 cells. Three×$10^5$ cells were seeded in plastic tissue culture flasks. Twenty-four hours later. Taurolidine was added to achieve final concentrations of 25 µM, 50 µM or 100 µM. Control cultures received an appropriate volume of Kollidine-17P. After an additional 24 h, cells were harvested and phosphotidylserine externalization determined by assessing Annexin-V FITC binding using cytofluorometric techniques. Each bar represents the mean±SE of four determinations. $p \leq 0.0$, ***$p \leq 0.001$

DNA cleavage into discrete fragments is a late event in the process of apoptosis. The appearance of DNA debris in the sub-$G_0/G_1$ region 48 h after Taurolidine exposure could be a reflection of apoptosis-associated DNA fragmentation. To evaluate this possibility, studies next assessed the ability of Taurolidine to increase phosphotidylserine externalization on cell membranes, an event that occurs earlier in the apoptotic process. These studies were fluorocytometry-based and employed a florescent antibody-binding assay (Annexin-V) to assess phosphotidylserine externalization. The results of the studies (shown in FIG. 3) revealed that in both the PA-1 and SKOV-3 human ovarian tumor cell lines a 24 h exposure to Taurolidine induced a significant, Taurolidine-concentration dependent, increase in Annexin-V binding of 4- and 3-fold, respectively. In contrast, in NIH-3T3 cells, Taurolidine exposure resulted in a non-significant increase (~5%) in antibody binding. These data supported the results from the cell cycle studies as well as the observation that Taurolidine exposure induced apoptosis in PA-1 and SKOV-3 cells, but not in NIH-3T3 cells. The results indicate that Taurolidine preferentially induces apoptosis (and apoptotic death) in tumor cells compared to in non-tumor cells.

Figure 4:
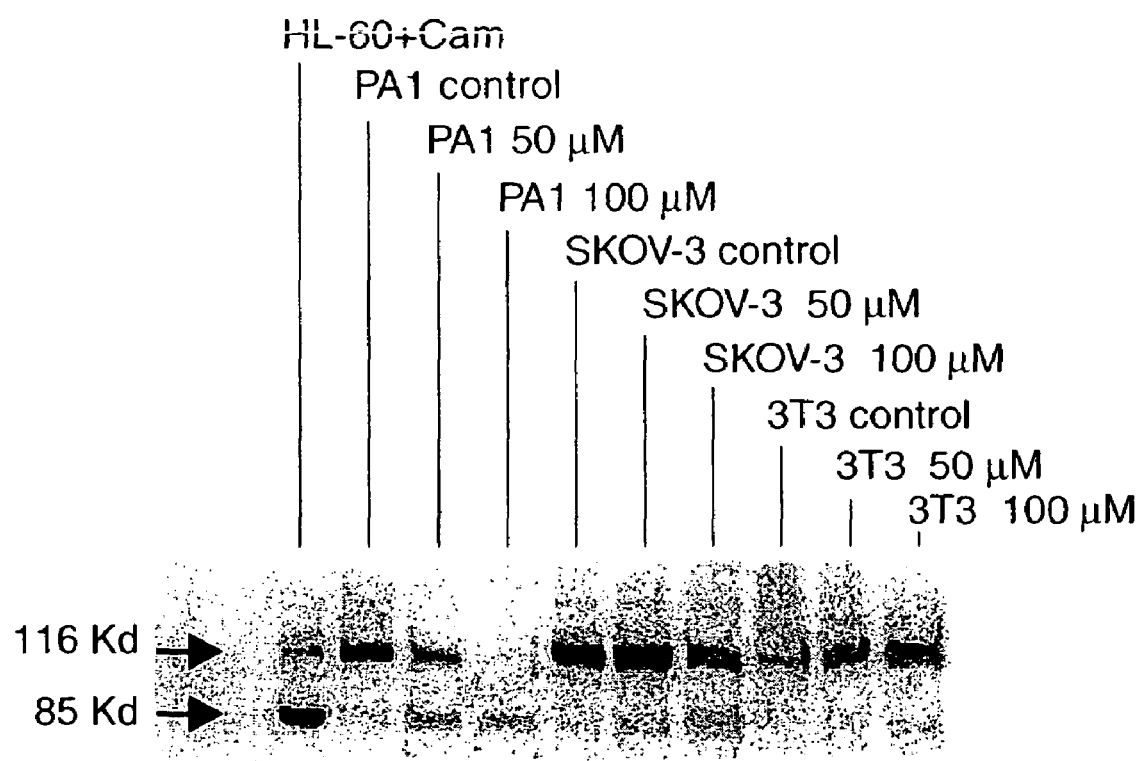
FIG. 4 is a photograph of showing the results of a Western-blot analysis of the effect of a 24 h exposure to 50 or 100 µM Taurolidine on PARP expression and the appearance of a major PARP cleavage product in PA-1, SKOV-3 and NIH-3T3 cells. Two×$10^6$ cells were seeded in 150 $cm^2$ tissue culture flasks. Twenty-four hours later, Taurolidine was added at concentrations of 50 µM or 100 µM. After an additional twenty-four hours, cells were harvested, cell number determined, and aliquots derived from equal cell numbers generated from each exposure condition. Total proteins from these whole cell lysates were separated by SDS-PAGE and transferred to nitrocellulose filters. Filters were then immunoblotted to detect intact PARP protein and cleavage fragments by using the clone C-2-10 mouse monoclonal anti-PARP antibody (Zymed Laboratories, San Francisco, Calif.). The resulting protein-antibody complexes were visualized by chemiluminescence techniques.

To further confirm the induction of apoptosis by Taurolidine, the relationship between Taurolidine exposure and PARP cleavage was assessed. PARP is a nuclear protein that plays a key role in the recognition and repair of both single and double strand DNA breaks. In addition, a key event in the apoptotic process is the cleavage, mediated by caspase 3 and caspase 9, and consequent catalytic deactivation of this protein. To determine if Taurolidine exposure resulted in PARP cleavage in ovarian tumor cells, Western-blot analysis was carried out on whole cell extracts of PA-1, SKOV-3 and NIH-3T3 cells following a 24 h exposure to either 50 or 100 μM Taurolidine. The results of this analysis, presented in the representative Western-blot contained in FIG. 4, revealed that in PA-1 and SKOV-3 cells exposure to either 50 μM or 100 μM Taurolidine resulted in PARP cleavage. In contrast, in NIH-3T3 cells, following exposure to Taurolidine there was little evidence of this proteolytic event. These data confirm that Taurolidine induces apoptosis in tumor cells but not in non-tumor cells.

Given the preferential induction of apoptotic death in tumor cells compared to normal nonneoplastic cells. Taurolidine was administered to tumor-bearing animals to further evaluate antineoplastic activity. Studies were initiated to evaluate the antineoplastic activity of taurolidine in nude mice bearing i.p. human ovarian tumor xenografts. In vivo studies were designed to identify the maximally tolerated dose (MTD) regimen of Taurolidine in nude female mice and to assess toxicity. Toxicity was evaluated by measuring changes in body weight, and mortality after a 3 d i.p. bolus injection regimen. Daily 1 ml injections delivered doses that ranged from 5 mg/mouse/day-30 mg/mouse/day. The results of these studies revealed that at daily doses below 15 mg/mouse (~650 mg/kg) Taurolidine were well-tolerated (Table 7).

Taurolidine-induced toxicity in athymic (nude) female mice was evaluated as follows. Groups of 5-10 mice were injected with Taurolidine on three consecutive days. Taurolidine doses evaluated ranged from 5-30 mg/mouse/injection and were delivered intraperitoneally in a volume of 1 ml (with the exception of the 25 and 30 mg doses, which, due to limited solubility, were delivered in a volume of 1.25 and 1.5 ml, respectively). During the injection regimen, and daily thereafter for 30 d, mice were weighed and examined. Experiments were repeated a minimum of three times and mortality and weight loss data pooled.

TABLE 7

| Taurolidine dose (mg/mouse/inj) | n | weight loss (nadir %) | mortality (%) |
|---|---|---|---|
| None (vehicle control) | 24 | −1.2 | 0 |
| 5 | 17 | −1.2 | 0 |
| 10 | 17 | −1.7 | 6% |
| 15 | 17 | −7.1 | 0 |
| 20 | 46 | −12.2 | 13% |
| 25 | 17 | −16.3 | 47% |
| 30 | 10 | −24.5 | 100% |

Maximum body weight loss as a result of this dose regimen was 7% and body weight returned to pre-injection levels within seven days after completion of the injection regimen. With regimens employing doses of 20 mg/mouse or greater, more significant toxicity was observed (Table 3). Specifically, nadir weight loss for regimens employing 20, 25 or 30 mg/mouse were −12%, −16% and −25%. respectively. Additionally, these Taurolidine dose regimens resulted in 15%, 43% and 100% mortality. respectively.

Figure 5:
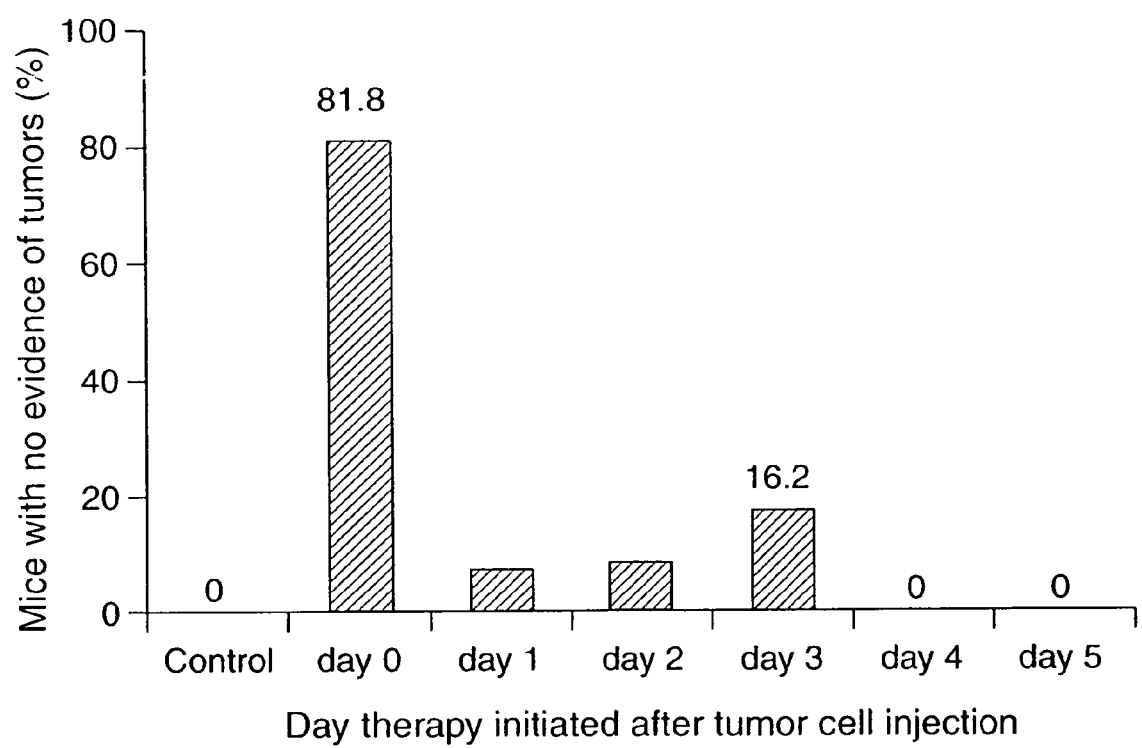
FIG. 5 is a bar graph showing the effect of delayed administration of a single 3 d i.p. bolus injection regimen of Taurolidine (20 mg/mouse/injection) on the occurrence of i.p. human tumor xenografts in female nude mice following the i.p. administration of 5×$10^6$ SKOV-3 human ovarian tumor cells. Taurolidine therapy was initiated on the day of tumor cell inoculation or up to 5 d thereafter. Fourteen days following the final Taurolidine injection, mice in all groups were sacrificed and the peritoneal cavity examined for the presence of tumors. Each experimental was repeated three times and the pooled number of animals in each group ranged from 15-21.
Figure 6:
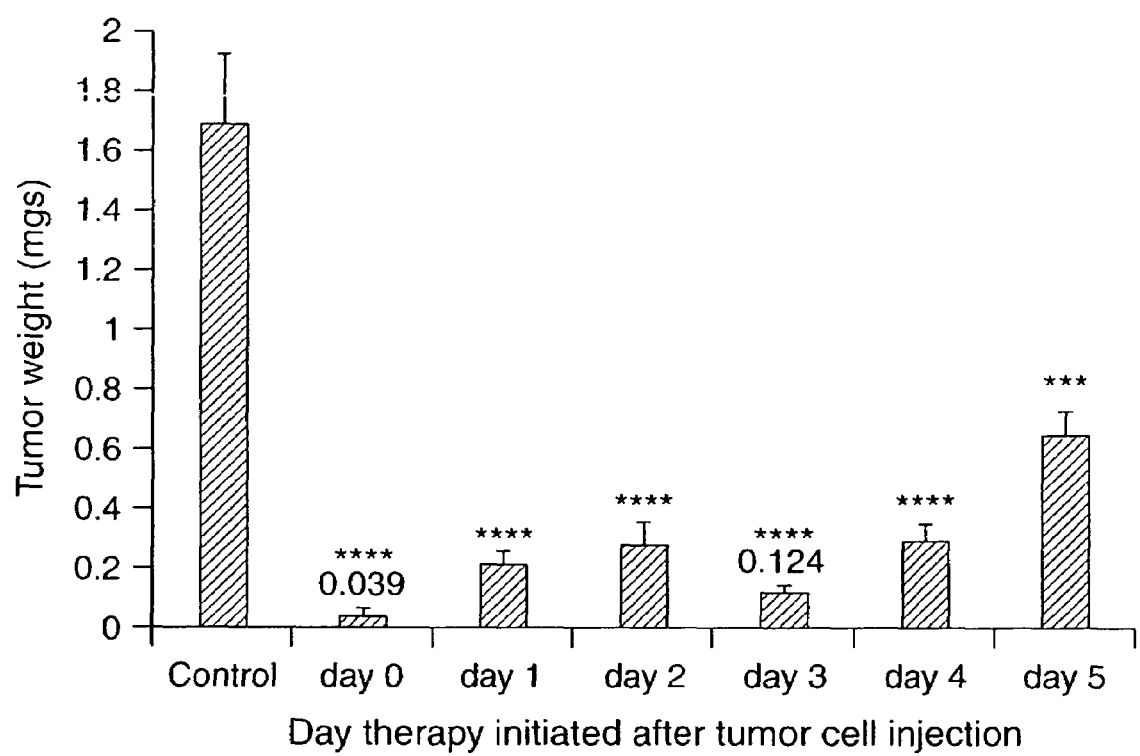
FIG. 6 is a bar graph showing the effect of delayed administration of a single 3 d i.p. bolus injection regimen of Taurolidine (20 mg/mouse/injection) on the weight of i.p. human tumor xenografts in female nude mice following the i.p. administration of 5×$10^6$ SKOV-3 human ovarian tumor cells. Taurolidine therapy was initiated on the day of tumor cell inoculation or up to 5 d thereafter. Fourteen days following the final Taurolidine injection, mice in all groups were sacrificed, i.p. ovarian tumor xenografts removed and tumor weighed. Each experiment was repeated three times and the pooled number of animals in each group ranged from 15-21. Each bar represents the mean (±SE) tumor weight of 15-21 animals. *$p \leq 0.001$, **$p \leq 0.0001$.

Based on the toxicity studies, a 3 daily 1 ml i.p. injection of Taurolidine, at a dose of 20 mg/mouse, was chosen to be the MTD. Studies next evaluated the antineoplastic activity of this regimen in mice bearing i.p. human ovarian tumor xenografts derived from the SKOV-3 cell line. Mice were injected i.p. with 5×10⁶ SKOV-3 cells. Taurolidine therapy, employing the 3 d 20 mg/mouse dose regimen, was initiated up to 5 d after tumor cell injection. Fourteen days following the termination of Taurolidine therapy, mice were sacrificed and all i.p. tumors removed and weighed. The results of this study, summarized in FIGS. 5 and 6, revealed that, when initiated on the day of tumor cell injection, Taurolidine therapy was highly effective and inhibited tumor formation (FIG. 5), ascites development, and growth (FIG. 6).

The effect of a single 3 d i.p. bolus injection regimen of Taurolidine (20 mg/mouse/injection, starting on the day of tumor cell injection) on the gross appearance of mice bearing i.p. xenografts of SKOV-3 human ovarian tumor cells was evaluated. Nineteen days after tumor cell injection, the mean tumor weight in control mice (no Taurolidine) was approximately 1.7 gm. Additionally, control animals were found to contain up to 7 ml of ascites fluid. Mean tumor weight in the taurolidine-treated group (single regimen of taurolidine) was less than 50 mgs and there was no evidence of ascites formation. A significant number of these Taurolidine-treated animals also were found to be tumor-free.

When therapy was initiated on the day of tumor cell injection, ~80% of treated mice had no evidence of disease upon sacrifice. Further, the mean tumor size in treated mice with tumors was approximately 40-fold smaller and in control (vehicle-treated) mice. Even if Taurolidine therapy was delayed for up to 3 d after tumor cell injection, approximately 10 percent of mice ere tumor free upon sacrifice and the mean tumor size in treated mice again was significantly smaller than in controls. The initiation of this single cycle of Taurolidine therapy 5 d after tumor cell injection (i.e., in mice with established i.p. ovarian tumors) as still capable of significantly inhibiting tumor growth.

The data presented herein indicate that a class of compounds exemplified by taurolidine possesses potent antineoplastic activity by selectively inhibiting tumor cell growth and specifically induce apoptosis in tumor cells. Surprisingly, the cytotoxic $IC_{50}$ of Taurolidine was found to be in the 10-50 µM range, approximately 100-fold lower that that required for its antibiotic effects. This difference in effective concentrations, combined with Taurolidine's observed low clinical toxicities indicates that this class of compounds is useful as a safe, clinically well-tolerated antineoplastic.

The data revealed that exposure to Taurolidine effectively inhibited the proliferation and viability of all tumor cell lines evaluated in a broad panel of solid tumor cell lines. Taurolidine induced apoptosis in neoplastic cells, indicating that its mechanism of action is not simply an inhibition of cell surface adhesion components or processes. Results of studies carried out in non-adherent cancer cell models support the above findings and reveal that as little as a 90 min exposure to Taurolidine induces apoptosis in the HL-60 human promyelocytic cell line. Exposure to Taurolidine results in the activation of caspases 3, 8 and 9, a disruption of mitochondrial membrane integrity accompanied by cytochrome-C efflux from these organelles, and the cleavage of PARP protein.

Human leukemia HL-60 cells, which were genetically-engineered to resist apoptotic induction, were induced to apoptosis independently (downstream) of the bcl-2/bax (anti-death gene) point in the signal transduction cascade. Surprising, in Bcl2-over expressing HL-60 cells. Taurolidine exposure was found to be capable of inducing apoptosis, but with a delayed onset. These data indicate that an active Taurolidine breakdown product is capable of reacting with membrane components to affect intracellular signaling processes and initiate the apoptosis process.

The ability of Taurolidine to induce apoptosis was found to be specific for tumor cells. This observation was confirmed using normal (non-tumor) primary cells derived from animals, which are known to be free of tumors. The cytotoxic and apoptotic activity of Taurolidine in normal murine bone marrow cultures as well as in activated human T-cell cultures was evaluated. In both normal cell models. Taurolidine was not cytotoxic in the high µM range and did not produce cellular changes consistent with the induction of apoptosis. In normal murine bone marrow, concentrations in the mM range were required to inhibit cell proliferation. These findings indicate that Taurolidine (or one of its metabolites) access a tumor-cell specific target capable of inducing tumor cell apoptosis.

EXAMPLE 2

Clinical Use

Taurolidine was administered by i.p. lavage immediately following surgery for removal of recurrent ovarian tumors. For patients with glioblastoma, taurolidine was administered systemically. To date, Taurolidine has been well tolerated in these patients.

Four patients. which were diagnosed with advanced recurrent glioblastoma multiforma, were treated with taurolidine. The prognosis for this group of patients was determined to be approximately 8 weeks of survival. Each patient received at least one 5 week regimen in which 20 g of taurolidine was infused intravenously into the arm over a period of 6 hours twice a week. In 3 out of the 4 patients treated, the tumor mass decreased or stayed the same; and in one case, a slight increase was seen. At 14 weeks after the initiation of therapy, each of the patients remains alive, having exceeded the 8 week prognosis. A beneficial clinical effect was achieved in these brain tumor patients with systemic administration of taurolidine, indicating that taurolidine, or a metabolite of taurolidine, successfully crossed the blood-brain barrier to gain access to the tumor in the brain.

These data indicate that taurolidine and derivatives and metabolites thereof are useful to inhibit or halt tumor growth and to extend the life expectancy of tumor patients.

Other embodiments are within the following claims.

What is claimed is:

1. A method of inhibiting growth of a recurrent autologous tumor in a mammal, comprising administering to said mammal after therapeutic intervention for a primary tumor a composition comprising taurolidine or a biologically active derivative thereof, in an amount sufficient to induce tumor cell death by apoptosis, wherein said tumor is ovarian cancer.

2. The method of claim 1, wherein said composition is administered to directly contact the surface of a cell of said recurrent tumor.

3. The method of claim 1, wherein said composition is administered by intraperitoneal lavage.

4. The method of claim 1, wherein said composition is administered systematically.

5. The method of claim 4, wherein said composition is administered intravenously.

6. The method of claim 1, wherein said composition comprises taurolidine.

7. The method of claim 1, wherein said composition comprises a taurolidine derivative or metabolite.

8. The method of claim 1, further comprising administering a chemotherapeutic agent selected from the group consisting of an antimetabolite, a purine or pyrimidine analogue, an alkylating agent, an intercalating agent, a crosslinking agent, and an antibiotic.

9. A method of inhibiting growth of a recurrent autologous tumor in a mammal, comprising administering to said mammal after therapeutic intervention for a primary tumor a composition comprising taurultam or a biologically active derivative thereof, in an amount sufficient to induce tumor cell death by apoptosis, wherein said tumor is ovarian cancer.

10. The method of claim 9, wherein said composition is administered to directly contact the surface of a cell of said recurrent tumor.

11. The method of claim 9, wherein said composition is administered by intraperitoneal lavage.

12. The method of claim 9, wherein said composition is administered systematically.

13. The method of claim 12, wherein said composition is administered intravenously.

14. The method of claim 9, wherein said composition comprises taurultam.

15. The method of claim 9, wherein said composition comprises a taurultam derivative.

16. The method of claim 9, further comprising administering a chemotherapeutic agent selected from the group consisting of an antimetabolite, a purine or pyrimidine analogue, an alkylating agent, an intercalating agent, a crosslinking agent, and an antibiotic.

17. The method of claim 1, wherein said composition consists of taurolidine and a pharmaceutically acceptable excipient.

18. The method of claim 1, wherein said composition consists of taurolidine, a chemotherapeutic agent, and a pharmaceutically acceptable excipient.

19. The method of claim 18, wherein said chemotherapeutic agent selected from the group consisting of an antimetabolite, a purine or pyrimidine analogue, an alkylating agent, an intercalating agent, a crosslinking agent, and an antibiotic.

20. The method of claim 9, wherein said composition consists of taurultam and a pharmaceutically acceptable excipient.

21. The method of claim 1, wherein said taurolidine is administered prophylactically at the time of surgery of said primary tumor.

22. The method of claim 9, wherein said composition consists of taurultam, a chemotherapeutic agent, and a pharmaceutically acceptable excipient.

23. The method of claim 22, wherein said chemotherapeutic agent selected from the group consisting of an antimetabolite, a purine or pyrimidine analogue, an alkylating agent, an intercalating agent, a crosslinking agent, and an antibiotic.

24. The method of claim 9, wherein said taurultam is administered. prophylactically at the time of surgery of said primary tumor.

* * * * *